US009034319B2

(12) United States Patent
Teichberg et al.

(10) Patent No.: US 9,034,319 B2
(45) Date of Patent: May 19, 2015

(54) METHODS OF TREATING CANCER OF THE CENTRAL NERVOUS SYSTEM

(75) Inventors: Vivian I. Teichberg, Savyon (IL); Angela Ruban-Matuzani, Rechovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 204 days.

(21) Appl. No.: 12/994,762

(22) PCT Filed: May 26, 2008

(86) PCT No.: PCT/IL2008/000711
§ 371 (c)(1),
(2), (4) Date: Nov. 25, 2010

(87) PCT Pub. No.: WO2009/144699
PCT Pub. Date: Dec. 3, 2009

(65) Prior Publication Data
US 2011/0070218 A1 Mar. 24, 2011

(51) Int. Cl.
*A61K 38/43* (2006.01)
*A61K 31/19* (2006.01)
*A61K 31/194* (2006.01)
*A61K 31/197* (2006.01)
*A61K 38/45* (2006.01)
*A61K 38/44* (2006.01)
*A61K 38/51* (2006.01)
*A61K 38/52* (2006.01)
*A61K 38/53* (2006.01)
*A61K 31/198* (2006.01)

(52) U.S. Cl.
CPC .............. *A61K 31/194* (2013.01); *A61K 38/44* (2013.01); *A61K 31/19* (2013.01); *A61K 38/51* (2013.01); *A61K 38/52* (2013.01); *A61K 38/45* (2013.01); *A61K 38/53* (2013.01); *A61K 31/198* (2013.01)

(58) Field of Classification Search
None
See application file for complete search history.

(56) References Cited

U.S. PATENT DOCUMENTS

| 6,133,317 | A | * | 10/2000 | Hart | 514/574 |
| 6,608,106 | B2 | * | 8/2003 | Agus et al. | 514/474 |
| 7,250,394 | B2 | * | 7/2007 | Nedergaard | 514/19.3 |
| 2003/0050224 | A1 | * | 3/2003 | Nedergaard | 514/1 |
| 2009/0304661 | A1 | * | 12/2009 | Teichberg et al. | 424/93.73 |
| 2011/0288070 | A1 | * | 11/2011 | Rogers et al. | 514/211.1 |

FOREIGN PATENT DOCUMENTS

| WO | WO 2004/012762 | 2/2004 |
| WO | WO 2006/066244 | 6/2006 |
| WO | WO 2007/105203 | 9/2007 |
| WO | WO 2007105203 A2 * | 9/2007 |
| WO | WO 2009/144699 | 12/2009 |

OTHER PUBLICATIONS

Rothstein et al. (2001) Nature Medicine 7(9): 994-995.*
Examination Report Dated Jun. 15, 2012 From the Instituto Mexicano de la Propiedad Industrial Re. Application No. MX/a/2010/012860 and Its Translation Into English.
International Preliminary Report on Patentability Dated Nov. 30, 2010 From the International Bureau of WIPO Re. Application No. PCT/IL2008/000711.
International Search Report and the Written Opinion Dated Aug. 22, 2008 From the International Searching Authority Re. Application No. PCT/IL2008/000711.
Rothstein et al. "Excitotoxic Destruction Facilitates Brain Tumor Growth", Nature Medicine, XP002490995, 7(9): 994-995, 2001. p. 994, Middle Col., Par.2, p. 995, Left Col., Par.1, p. 995, Right Col., Par.2.
Requisition by the Examiner Dated Mar. 26, 2014 From the Canadian Intellectual Property Office Re. Application No. 2,725,551.
Patent Examination Report Dated Jul. 26, 2013 From the Australian Government, IP Australia Re. Application No. 2008357095.
Patent Examination Report Dated Jan. 22, 2014 From the Australian Government, IP Australia Re. Application No. 2008357095.

* cited by examiner

*Primary Examiner* — Lisa J Hobbs

(57) ABSTRACT

A method of treating a cancer of the central nervous system in a subject in need thereof is provided. The method comprising administering to the subject a therapeutically effective amount of an agent which reduces blood glutamate levels and enhances brain to blood glutamate efflux to thereby treat the cancer of the central nervous system in the subject.

10 Claims, 2 Drawing Sheets
(2 of 2 Drawing Sheet(s) Filed in Color)

METHODS OF TREATING CANCER OF THE CENTRAL NERVOUS SYSTEM

RELATED APPLICATIONS

This Application is a National Phase of PCT Patent Application No. PCT/IL2008/000711 having International filing date of May 26, 2008. The contents of the above Application is incorporated herein by reference.

FIELD AND BACKGROUND OF THE INVENTION

The present invention, in some embodiments thereof, relates methods of treating cancer of the central nervous system.

Central nervous system malignant neoplasias and glioma in particular, have so far defied all current therapeutic modalities. In the last few years, an ever increasing body of data have suggested that glutamate (Glu), the major excitatory neurotransmitter in brain, plays a crucial role in the growth of malignant gliomas, their invasiveness and ability to destroy neighboring brain tissue (Lyons, et al. 2007; Sontheimer 2003) while being also the possible cause of the tumor-associated seizures that often occur in conjunction with gliomas.

Thus, studies with glioma cells in culture have shown that the cells release massive amounts of Glu resulting in elevations of the extracellular concentrations of Glu in excess of 100 µLM within hours in a space that is 1000-fold larger than the cellular volume (Ye and Sontheimer 1999). This massive release was attributed in part to a deficient Glu uptake by glioma cells attributed to the reduction-mislocalization of Glu transporters (Ye, et al. 1999). Moreover, exposure of cultured hippocampal neurons to glioma-conditioned medium caused widespread neuronal death attributed to the excitotoxic effects exerted by excess Glu (Ye and Sontheimer 1999). This neuronal death was inhibited by NMDA receptor antagonists as well as by inhibitors of the glutamate-cystine exchanger (Ye and Sontheimer 1999). The importance of this massive Glu release was explored in the context of glioma growth. It was found that increased peritumoral levels of Glu were present in the brain of rats implanted with RG2 glioma cells (Sheline, et al. 2000). Moreover, injection of C6 gliomas into rat brain striata yielded significant tumor growth only in glioma cells capable of releasing Glu (Takano, et al. 2001).

Additional findings showed that antagonists of the NMDA and AMPA receptors, two major subtypes of ionotropic Glu receptors, inhibited the proliferation (Rzeski, et al. 2002) and migration of both rat (Takano, et al. 2001) and human (Ishiuchi, et al. 2002) malignant gliomas while an antagonist of the Glu metabotropic receptor reduced glioma growth (Arcella, et al. 2005).

Several scientific reports suggested glutamate inhibitors for the treatment of gliomas include: Birmingham 2002; Ikonomidou and Turski 2002; Lutsep and Clark 2001a; Lutsep and Clark 2001b. Related patent literature include: U.S. Patent Application Number 20030050224.

PCT Publication Number WO2004/012762 teaches a method of reducing extracellular brain glutamate levels. The method comprises administering to a subject in need thereof a therapeutically effective amount of an agent capable of reducing blood glutamate levels thereby reducing extracellular brain glutamate levels. Other related publications include, Pawlik, et al. 1981, O'Kane, et al. 1999, Gottlieb, et al. 2003, (eichberg, et al. 2008 and Zlotnik, et al. 2008.

SUMMARY OF THE INVENTION

According to one aspect of the present invention there is provided a method of treating a cancer of the central nervous system in a subject in need thereof, the method comprising administering to the subject a therapeutically effective amount of an agent which reduces blood glutamate levels and enhances brain to blood glutamate efflux to thereby treat the cancer of the central nervous system in the subject.

According to one aspect of the present invention there is provided a use of an agent which reduces blood glutamate levels and enhances brain to blood glutamate efflux for treating a cancer of the central nervous system.

According to one aspect of the present invention there is provided an article-of-manufacture comprising packaging material and a pharmaceutical composition identified for treating a cancer of the central nervous system being contained within the packaging material, the pharmaceutical composition including, as an active ingredient, an agent capable of reducing blood glutamate levels and an anti cancer agent and a pharmaceutically acceptable carrier.

According to further features in some embodiments of the invention described below, the anti cancer agent comprises a chemotherapy.

According to still further features in the described exemplary embodiments the agent is at least one glutamate modifying enzyme and/or a modification thereof.

According to still further features in the described exemplary embodiments the at least one glutamate modifying enzyme is selected from the group consisting of a transaminase, a dehydrogenase, a decarboxylase, a ligase, an aminomutase, a racemase and a transferase.

According to still further features in the described exemplary embodiments the transaminase is selected from the group consisting of glutamate oxaloacetate transaminase, glutamate pyruvate transaminase, acetylornithine transaminase, ornithine-oxo-acid transaminase, succinyldiaminopimelate transaminase, 4-aminobutyrate transaminase, (s)-3-amino-2-methylpropionate transaminase, 4-hydroxyglutamate transaminase, diiodotyrosine transaminase, thyroid-hormone transaminase, tryptophan transaminase, diamine transaminase, cysteine transaminase, L-Lysine 6-transaminase, histidine transaminase, 2-aminoadipate transaminase, glycine transaminase, branched-chain-amino-acid transaminase, 5-aminovalerate transaminase, dihydroxyphenylalanine transaminase, tyrosine transaminase, phosphoserine transaminase, taurine transaminase, aromatic-amino-acid transaminase, aromatic-amino-acid-glyoxylate transaminase, leucine transaminase, 2-aminohexanoate transaminase, ornithine(lysine) transaminase, kynurenine-oxoglutarate transaminase, D-4-hydroxyphenylglycine transaminase, cysteine-conjugate transaminase, 2,5-diaminovalerate transaminase, histidinol-phosphate transaminase, diaminobutyrate-2-oxoglutarate transaminase, and udp-2-acetamido-4-amino-2,4,6-trideoxyglucose transaminase.

According to still further features in the described exemplary embodiments the dehydrogenase is a glutamate dehydrogenase.

According to still further features in the described exemplary embodiments the decarboxylase is a glutamate decarboxylase.

According to still further features in the described exemplary embodiments the ligase is a glutamate-ethylamine ligase.

According to still further features in the described exemplary embodiments the transferase is selected from the group consisting of glutamate N-acetyltransferase and adenylyltransferase.

According to still further features in the described exemplary embodiments the aminomutase is a glutamate-1-semialdehyde 2,1-aminomutase.

According to still further features in the described exemplary embodiments the agent is at least one co-factor of a glutamate modifying enzyme.

According to still further features in the described exemplary embodiments the co-factor is selected from the group consisting of oxaloacetate, pyruvate, $NAD^+$, $NADP^+$, 2-oxo-hexanedioic acid, 2-oxo-3-sulfopropionate, 2-oxo-3-sulfino-propionic acid, 2-oxo-3-phenylpropionic acid, 3-indole-2-oxopropionic acid, 3-(4-hydroxyphenyl)-2-oxopropionic acid, 4-methylsulfonyl-2-oxobutyric acid, 3-hydroxy-2-oxopropionic acid, 5-oxopentanoate, 6-oxo-hexanoate, glyoxalate, 4-oxobutanoate, α-ketoisocaproate, α-ketoisovalerate, α-keto-β-methylvalerate, succinic semialdehyde-(-4-oxobutyrate), pyridoxal phosphate, pyridoxal phosphate precursors and 3-oxoisobutanoate.

According to still further features in the described exemplary embodiments the agent comprises a glutamate modifying enzyme and a co-factor thereof.

According to still further features in the described exemplary embodiments the glutamate modifying enzyme comprises glutamate oxaloacetate transaminase and the co-factor thereof comprises oxaloacetate.

According to still further features in the described exemplary embodiments the glutamate modifying enzyme comprises pyruvate transaminase and the co-factor thereof comprises pyruvate.

According to still further features in the described exemplary embodiments the administering is effected at a concentration of the agent not exceeding 1 g/Kg body weight/hour.

According to still further features in the described exemplary embodiments the agent is at least one inhibitor of a glutamate synthesizing enzyme.

According to still further features in the described exemplary embodiments the inhibitor is selected from the group consisting of gamma-Acetylenic GABA, GABAculine, L-canaline, 2-amino-4-(aminooxy)-n-butanoic acid, 3-Chloro-4-aminobutanoate, 3-Phenyl-4-aminobutanoate, Isonicotinic hydrazide; (S)-3-Amino-2-methylpropanoate, Phenylhydrazine; 4-Fluorophenyl)alanine, Adipate, Azaleic acid, Caproate, 3-Methylglutarate, Dimethylglutarate, Diethylglutarate, Pimelate, 2-Oxoglutamate, 3-Methyl-2-benzothiazolone hydrazone hydrochloride, Phenylpyruvate, 4-hydroxyphanylpyruvate, Prephenate and Indole pyruvate.

According to still further features in the described exemplary embodiments the cancer is a glioma.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

The patent or application file contains at least one drawing executed in color. Copies of this patent or patent application publication with color drawing(s) will be provided by the Office upon request and payment of the necessary fee.

In the drawings:

FIG. 1 is a graph showing oxaloacetate effect on glioma cells in vitro.

Figure 2A:
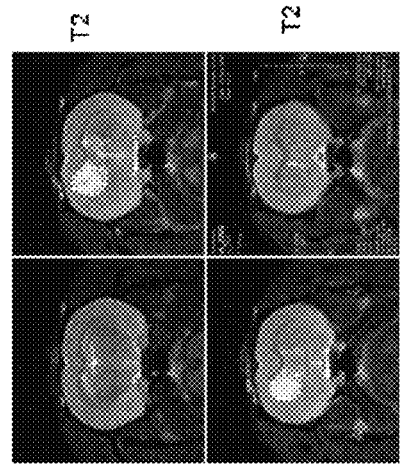
Figure 2B:
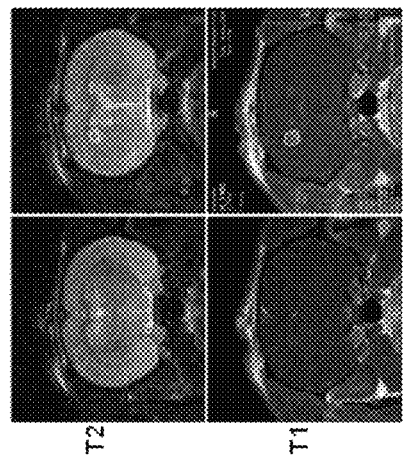

FIGS. 2a-b are magnetic resonance images of C6 glioma tumor cells implanted in the rat striatum. The T2 images illustrate serial coronal sections through the tumor. Parallel T1 images are shown on the left panel. As can be seen the tumor visualized on day 7 in a single brain section (FIG. 2A) appeared 10 days later in 2 sections out of the four sequential sections presented (FIG. 2B, note that only the T2 images are presented). The treatment started on day 7 comprised providing the rats with either 0.2M oxaloacetate (in tap water) or 0.4M NaCl (in tap water) in their drinking water. In control animals which were treated with drinking water alone, the tumor size was at least 10 times greater (not shown).

Figure 3:
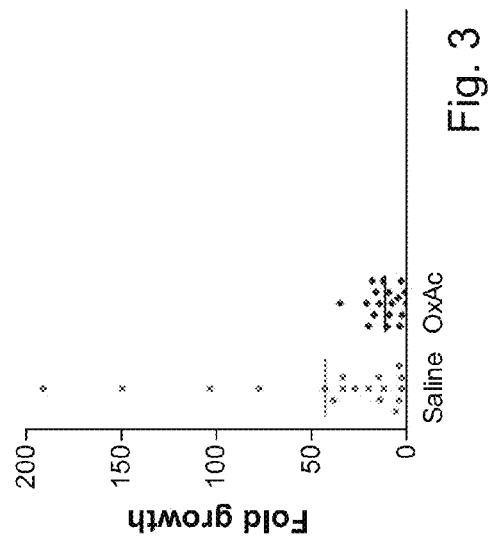

FIG. 3 is a graph showing glioma invasiveness in rats drinking 0.4 M NaCl (n=19, pink dots) and in rats drinking 0.2 M oxaloacetate (OxAc, n=19, blue dots). The tumor invasiveness was calculated by dividing the tumor size determined at the second MRI session by that measured 10 days earlier at the first MRI session. (unpaired student t test: p=0.02; F test to compare variances: p=0.001).

DESCRIPTION OF EMBODIMENTS OF THE INVENTION

The present invention, in some embodiments thereof, relates to methods of treating cancer of the central nervous system.

For purposes of better understanding some embodiments of the present

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing the present invention to practice, the present inventor uncovered that a blood glutamate scavenger which enhances brain-to-blood glutamate efflux can be used to inhibit the spread of tumor cells by preserving normal brain cells which would otherwise be damaged or killed by tumor-derived glutamate.

The present inventors hypothesized that since brain tumors are highly vascularized and brain capillary endothelial cells are involved in a brain-to-blood glutamate efflux, agents which are able to decrease blood glutamate levels that in-turn increase the driving force for the efflux of excess glutamate from brain into blood should also cause the elimination of peritumoral excess glutamate. Accordingly it was suggested that the elimination of peritumoral excess glutamate should impede the ability of the tumor to create the necessary space for its expansion in brain.

As is illustrated hereinbelow and in the Examples section which follows, oral administration of oxaloacetate into rats implanted with glioma cells slowed tumor cell spread, as evidenced by MRI analysis.

Thus, according to one aspect of the present invention there is provided a method of treating a cancer of the central nervous system in a subject in need thereof. The method comprising administering to the subject a therapeutically effective amount of an agent which reduces blood glutamate levels and enhances brain to blood glutamate efflux and treat the cancer of the central nervous system in the subject.

As used herein the phrase "cancer of the central nervous system" refers to a brain tumor (primary or secondary), which typically releases glutamate at levels sufficient to allow glutamate to exert excitotoxicity on neighboring healthy neuronal cells. Thus, a cancer of the central nervous system include, primary tumors of glial, neuronal, schwann cell, pinealcyte, menningioma and melanoma, as well as sarcoma, lymphoma and multiple systemic malignancies that metastasize in the brain.

Specific examples include, but are not limited to, astrocytoma and glioblastoma, and also their related neural and glial tumors, glioma (e.g., which include grades 1 and 2), oligodendroglioma, neurocytoma, dysplastic neuroepithelial tumor, primitive neuroectodermal tumor, and ganglioneuroma.

Other types of cancer which can be treated in accordance with the present teachings, can be identified using methods which are well known in the art. For example, EAAT2 promoter activity assay, glutamate toxicity assay (e.g., co-culturing with neurons followed by assaying cell killing), expression of glutamate cysteine exchanger glutamate transporters (e.g., GCG, EAAC1, the latter as exemplified by U.S. Patent Application Number 20030050224, which is hereby incorporated by reference). Alternatively, other cancers which can be subject to the present treating modalities can be those in which glutaminergic etiology of intractable seizures and/or secondary brain atrophy, by induction of apoptotic mechanisms is observed.

As used herein the term "treating" refers to abrogating, substantially inhibiting, slowing or reversing the progression of cancer of the central nervous system, substantially ameliorating clinical or aesthetical symptoms of a cancer of the central nervous system or substantially preventing the appearance of clinical or aesthetical symptoms of a cancer of the central nervous system. In a specific embodiment the term treating refers to inhibiting or slowing spreading (i.e., growth) of a tumor of the central nervous system.

An agent, which is capable of reducing blood glutamate according to this aspect of the present invention includes any glutamate modifying enzyme and/or a co-factor thereof or any artificially modified derivatives (e.g. esters).

Enzymes that use glutamate as a substrate follow the general formula:

A+GLUTAMATE←(enzyme)→C+D whereby A represents the co-substrate, ←(enzyme)→symbolizes a reversible enzyme and C and D are metabolites of the enzyme. Examples illustrated by this formula include: Glutamate+oxaloacetate←(GOT)→2-keto-glutarate+aspartate, Glutamate+pyruvate←(GPT)→2-keto-glutarate+alanine or Glutamate+4-methyl-2-oxopentoate←(branched-chain-amino-acid transaminase)→2-ketoglutarate+Valine.

Examples for different substrates that work on the same enzyme include Glutamate+2-oxohexanedioic acid←(GOT)→2-keto-glutarate+2-aminohexanedioic acid. Glutamate+2-oxo-3-phenylpropionic acid←(GOT)→2-keto-glutarate+phenylalanine. Glutamate+3-hydroxy-2-oxopropionic acid←(GOT)→2-keto-glutarate+serine. Glutamate+5-oxopentanoate←(GPT)→2-keto-glutarate+5-aminopentanoate. Glutamate+4-oxobutanoate←(GPT)→2-keto-glutarate+4-aminobutanoate. Glutamate+glyoxalate←(GPT)→2-ketoglutarate+glycine.

The conversion of glutamate to 2-ketoglutarate is reversible. Thus, upon glutamate transformation via an enzymatic reaction into 2-ketoglutarate, there is a buildup of 2-ketoglutarate which can cause the enzyme to work in the reverse direction and convert 2-ketoglutarate into glutamate. It is therefore beneficial to further break down 2-ketoglutarate and in this way ensure the continual metabolism of glutamate. One such enzyme that metabolizes 2-ketoglutarate is 2-ketoglutarate dehydrogenase through the general reaction-2-ketoglutarate+lipoamide←(2-ketoglutarate dehydrogenase)→S-succinyldihydrolipoamide+$CO_2$.

Thus, as used herein "a glutamate modifying enzyme" is an enzyme, which utilizes glutamate as a substrate and produces a glutamate reaction product. A glutamate modifying enzyme can be a natural occurring enzyme or an enzyme which has been modified to obtain improved features, such as higher affinity to glutamate than to a modified glutamate, stability under physiological conditions, solubility, enhanced enantioselectivity, increased thermostability and the like as is further described hereinunder.

Numerous glutamate modifying enzymes are known in the art. For example, transaminases, which play a central role in amino acid metabolism and generally funnel α-amino groups from a variety of amino acids via the coupled conversion of glutamate into α-ketoglutarate or of α-ketoglutarate into glutamate.

Examples of transaminases include but are not limited to glutamate oxaloacetate transaminases, glutamate pyruvate transaminases, acetylornithine transaminases, ornithine-oxo-acid transaminases, succinyldiaminopimelate transaminases, 4-aminobutyrate transaminases, alanine transaminases (note: same as glutamate pyruvate transaminases, (s)-3-amino-2-methylpropionate transaminases, 4-hydroxyglutamate transaminases, diiodotyrosine transaminases, thyroid-hormone transaminases, tryptophan transaminases, diamine transaminases, cysteine transaminases, L-Lysine 6-transaminases, histidine transaminases, 2-aminoadipate transaminases, glycine transaminases, branched-chain-amino-acid transaminases, 5-aminovalerate transaminases, dihydroxyphenylalanine transaminases, tyrosine transaminases, phosphoserine transaminases, taurine transaminases, aromatic-amino-acid transaminases, aromatic-amino-acid-glyoxylate transaminases, leucine transaminases, 2-aminohexanoate transaminases, ornithine (lysine) transaminases, kynurenine-oxoglutarate transaminases, D-4-hydroxyphenylglycine transaminases, cysteine-conjugate transaminases, 2,5-diaminovalerate transaminases, histidinol-phosphate transaminases, diaminobutyrate-2-oxoglutarate transaminases, UDP-2-acetamido-4-amino-2,4,6-trideoxyglucose transaminases and aspartate transaminases.

Other examples of glutamate modifying enzymes include but are not limited to glutamate dehydrogenases, which generate ammonium ion from glutamate by oxidative deamination; decarboxylases such as glutamate decarboxylase; ligases such as glutamate-ethylamine ligase, glutamate-cysteine ligase; transferases such as glutamate N-acetyltransferase and N2-acetyl-L-ornithine, adenylyltransferase; aminomutases such as glutamate-1-semialdehyde 2,1-aminomutase and glutamate racemase [Glavas and Tanner (2001) Biochemistry 40(21):6199-204)].

It will be appreciated that artificially modified enzymes can also be used according to this aspect of the present invention.

Modification of enzymes can be effected using numerous protein directed evolution technologies known in the art [for review see Kuchner and Arnold (1997) TIBTECH 15:523-530; Furukawa J. Bacteriol. 2004 August; 186(16):5189-96].

Typically, directed enzyme evolution begins with the creation of a library of mutated genes. Gene products that show improvement with respect to the desired property or set of properties are identified by selection or screening, and the gene(s) encoding those enzymes are subjected to further cycles of mutation and screening in-order to accumulate beneficial mutations. This evolution can involve few or many generations, depending on the progress observed in each generation.

Preferably, for successful directed evolution a number of requirements are met; the functional expression of the enzyme in a suitable microbial host; the availability of a screen (or selection) sensitive to the desired properties; and the identification of a workable evolution strategy.

Examples of mutagenesis methods which can be used in enzyme directed evolution according to this aspect of the present invention include but are not limited to UV irradiation, chemical mutagenesis, poisoned nucleotides, mutator strains [Liao (1986) Proc. Natl. Acad. Sci. U.S.A 83:576-80], error prone PCR [Chen (1993) Proc. Natl. Acad. Sci. U.S.A 90:5618-5622], DNA shuffling [Stemmer (1994) Nature 370: 389-91], cassette [Strausberg (1995) Biotechnology 13:669-73], and a combination thereof [Moore (1996) Nat. Biotechnol. 14:458-467; Moore (1997) J. Mol. Biol. 272:336-347].

Screening and selection methods are well known in the art [for review see Zhao and Arnold (1997) Curr. Opin. Struct. Biol. 7:480-485; Hilvert and Kast (1997) Curr. Opin. Struct. Biol. 7:470-479]. Typically, selections are attractive for searching larger libraries of variants, but are difficult to device for enzymes that are not critical to the survival of the host organism. Further more, organisms may evade imposed selective pressure by unexpected mechanisms. Less stringent functional complementation can be useful in identifying variants which retain biological activity in libraries generated using relatively high mutagenic rates [Suzuki (1996) Mol. Diversity 2:111-118; Shafikhani (1997) Biol. Techniques 23:304-310; Zhao and Arnold (1997) Curr. Opin. Struct. Biol. 7:480-485].

As described hereinabove, the agent according to this aspect of the present invention, can include one or more co-factors of glutamate modifying enzymes, which can accelerate activity of the latter ($V_{max}$). These can be administered in order to enhance the rate of endogenous glutamate modifying enzymes or in conjunction with glutamate modifying enzymes (described hereinabove).

Co-factors of glutamate-modifying enzymes include but are not limited to oxaloacetate, pyruvate, $NAD^+$, $NADP^+$, 2-oxohexanedioic acid, 2-oxo-3-sulfopropionate, 2-oxo-3-sulfinopropionic acid, 2-oxo-3-phenylpropionic acid, 3-indole-2-oxopropionic acid, 3-(4-hydroxyphenyl)-2-oxopropionic acid, 4-methylsulfonyl-2-oxobutyric acid, 3-hydroxy-2-oxopropionic acid, 5-oxopentanoate, 6-oxo-hexanoate, glyoxalate, 4-oxobutanoate, α-ketoisocaproate, α-ketoisovalerate, α-keto-β-methylvalerate, succinic semialdehyde (4 oxobutyrate), 3-oxoisobutanoate, pyridoxal phosphate, 5-oxopentanoate, 6-oxohexanoate and their artificially modified derivatives (e.g., esters).

Since modified glutamate (i.e., glutamate reaction product) can be reversibly modified (i.e., interconverted) to glutamate, the agent, according to this aspect of the present invention, preferably includes a modified glutamate converting enzyme which is incapable of converting the modified glutamate back into glutamate to thereby insuring continual metabolism of glutamate.

Examples of modified or modifiable glutamate converting enzymes include but are not limited to GPT, GOT, Glutamate decarboxylase and glutamate dehydrogenase.

Modified glutamate converting enzymes can also include glutamate modifying enzymes artificially modified to possess lower affinity for glutamate reaction product than for glutamate. For example, the E. coli GOT (GenBank Accession No. D90731.1) is characterized by an affinity for glutamate of about 8 mM and an affinity for 2-ketoglutarate of about 0.2 mM. A human enzyme or a humanized enzyme characterized by such affinities is preferably used according to this aspect of the present invention such as described by Doyle et al. in Biochem J. 1990 270(3):651-7.

Optionally, co-factors of modified glutamate converting enzymes can be included in the agent according to this aspect of the present invention. Examples of co-factors of modified glutamate converting enzymes include but are not limited to lipoic acid and its precursors, thiamine pyrophosphate and its precursors, pyridoxal phosphate and its precursors and the like.

It will be appreciated that the agent according to this aspect of the present invention may also include inhibitors of glutamate synthesizing enzymes (e.g., phosphate activated glutaminase). Numerous inhibitors of glutamate producing enzymes are known in the art. Examples include but are not limited gabapentin which has been shown to modulate the activity of branched chain aminotransferases [Taylor (1997) Rev. Neurol. 153(1):539-45] and aspirin at high doses (i.e., 4-6 g/day) a neuroprotective drug against glutamate excitotoxicity [Gomes (1998) Med. J. India 11:14-17]. Other inhibitors may be identified in the publicly available BRENDA, a comprehensive enzyme information system [www.brenda.uni-koeln.de/]. Examples include but are not limited to, gamma-Acetylenic GABA, GABAculine, L-canaline, 2-amino-4-(aminooxy)-n-butanoic acid; 3-Chloro-4-aminobutanoate; 3-Phenyl-4-aminobutanoate; Isonicotinic hydrazide; (S)-3-Amino-2-methylpropanoate; Phenylhydrazine; 4-Fluorophenyl)alanine; Adipate, Azelaic acid, Caproate, 3-Methylglutarate, Dimethylglutarate, Diethylglutarate, Pimelate, 2-Oxoglutamate; 3-Methyl-2-benzothiazolone hydrazone hydrochloride; Phenylpyruvate, 4-Hydroxyphenylpyruvate, Prephenate, Indole pyruvate and their artificially modified derivatives (e.g., esters). Although each of the components described hereinabove may comprise the agent of the present invention, it will be appreciated that for optimal blood-glutamate reducing activity, the agent may include a combination of the above described components (i.e., glutamate modified enzyme, co-factor thereof, modified glutamate converting enzyme and co-factor thereof).

For example, co-factor molecules e.g., oxaloacetate, reaching the blood system may be absorbed into tissues via the ubiquitously distributed transporters (e.g., dicarboxylate transporters). Thus, in the case of oxaloacetate, the blood glutamate scavenging ability of oxaloacetate relies mainly on the levels of the glutamate-oxaloacetate transaminase (GOT) present in blood. Increasing the blood GOT concentration by the systemic (e.g., intravenous) administration of recombinant GOT can thus be expected to significantly improve the blood glutamate scavenging property of oxaloacetate. The latter effect should also benefit from a more effective administration of oxaloacetate in order to reach higher and steady levels of blood plasma oxaloacetate.

Thus, according to exemplary embodiments of this aspect of the present invention the agent includes oxaloacetate and pyruvate. Preferably, the agent is administered at a dose not exceeding 1 g/kg×hour.

In some cases, the agent administered is modified in order to increase the therapeutic effect or reduce unwanted side effects. For example, administration of oxaloacetate diethyl-ester is favorable over administration of oxaloacetate alone since oxaloacetate exerts its therapeutic potential at relatively high concentrations and requires full titration of its carboxyl moieties with sodium hydroxide at 3:1 stoichiometric ratio which presents unacceptable electrolyte load above safe levels.

Alternatively or additionally, to increase the life-time of the enzyme in the blood, the present invention also envisages repetitive administration of the enzyme (e.g., on a monthly basis), use of reagents which will increase the life-time in the circulation e.g., PEGylated enzyme, or the entrapment of the enzyme in suitable carriers that should cause a sustained increase of blood enzyme levels allowing an effective blood glutamate scavenging with lower concentrations of the cofactor.

Alternatively, recombinant or purified enzymes of the present invention may be attached to a heterologous polypeptide that increases the half-life of the enzyme in the serum. Examples of heterologous amino acid sequences that may be used in accordance with the teachings of the present invention include, but are not limited to, immunoglobulin, galactosidase, glucuronidase, glutathione-S-transferase (GST), carboxy terminal peptide (CTP) from chorionic gonadotrophin (CG☐) and chloramphenicol acetyltransferase (CAT) [see for example U.S. Publication No. 20030171551].

The agent can be administered to a subject using any one of several suitable administration modes which are further described hereinbelow with respect to the pharmaceutical compositions of the present invention.

The agent utilized by the method of the present invention can be administered to an individual subject per se, or as part of a pharmaceutical composition where it is mixed with a pharmaceutically acceptable carrier.

As used herein a "pharmaceutical composition" refers to a preparation of one or more of the active ingredients described hereinabove along with other components such as physiologically suitable carriers and excipients, penetrants etc. The purpose of a pharmaceutical composition is to facilitate administration of a compound to an organism.

Herein the term "active ingredient" refers to the preparation accountable for the biological effect (e.g., the glutamate modifying enzyme, and/or cofactors thereof).

Hereinafter, the phrases "physiologically acceptable carrier" and "pharmaceutically acceptable carrier" are interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration of the pharmaceutical composition of the present invention may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, intraosseus and intraocular injections.

Preferred is a systemic mode and dosing that reduces blood (plasma) glutamate levels and enhances brain-to-blood glutamate levels.

The administration mode may also depend on the status of the patient. For example, in case of a seizure, intraosseus administration or intravenal administration may be preferred.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any pharmaceutical composition used by the treatment method of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Animal models for cancer of the nervous system are readily available.

Thus, xenograft models are well suited for evaluating dose response characteristics of preclinical therapies, and for assessing the influence of tumor site on therapeutic response.

Weissenberger et al J. Neurosurg. 2007 April; 106(4):652-9 have produced germline insertion of a transgene expressing v-src from the GFAP promoter (limiting the expression to astrocytes) resulting in the formation of astrocytomas. V-src activates several signal transduction pathways that are also activated in human gliomas. These GFAP/v-src gliomas are primarily either low grade or anaplastic but in some cases acquire the histologic characteristics of glioblastomas.

Guha et al. Am J Pathol. 2005 September; 167(3):859-67 have developed transgenic mice which over-expressed oncogenic H-Ras from the GFAP promoter as. Different founder lines of these mice express various levels of oncogenic Ras. The highest producers of H-Ras develop astrocytomas with all the characteristics of glioblastomas. The moderate H-Ras expressors go on to germline transmission and develop low grade and anaplastic astrocytomas with high prevalence by 3 months of age.

Reilly et al. Nat. Genet. 2000 September; 26(1):109-13 have generated gliomas with astrocytic character with a combined deletion of Nf-1 and p53. Nf-1 is a RasGAP protein that down regulates Ras activity therefore, loss of Nf-1 results in elevated Ras activity. Alone, mutation of Nf-1 in all cells within the mouse results in astrogliosis, but not glioma formation; however, when combined with mutations of p53, mice develop astrocytic tumors with characteristics of glioblastomas in humans.

Retroviral vector gene transfer of PDGF-B to somatic cells has been used to generate astrocytic gliomas by Uhrbom et al. Nat. Med. 2004 November; 10(11):1257-60 In these experiments, replication-competent MMLV vector systems result in the formation of various CNS tumor morphologies. The most frequent histology seen in these experiments are high grade gliomas with characteristics of glioblastomas.

Somatic-cell gene transfer with tissue-specific ALV based RCAS retroviral vectors also show the formation of glioblastomas in mice. These tumors arise after combined gene transfer of genes encoding activated Ras and Akt to nestin expressing CNS progenitors. In this system, neither Ras nor Akt alone are sufficient for the generation of these glioblastomas.

A transgenic mouse model with features of human WHO grade III astrocytoma was developed by astrocyte-specific inactivation of pRb and related proteins, p107 and p130 (Xiao et al., 2002). This was accomplished by expression of a single copy of the T121 gene driven by the GFAP promoter. T121 is a 121-amino acid N-terminal fragment of SV40 T antigen that dominantly inactivates the pRb proteins, but does not interfere with p53 function. One hundred percent of TgG(Z) T121 mice develop high grade astrocytoma at around 6 months of age. Histologic features resembling the human disease include adhesion to neurons and vasculature.

The Examples section, which follows provides further guidance as to suitable dosages.

Depending on the severity and responsiveness of the condition to be treated, dosing can be of a single or a plurality of administrations, with course of treatment lasting from several days to several weeks or until cure is effected or diminution of the disease state or symptoms is achieved.

The amount of the pharmaceutical composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It will be appreciated that the present agents can be provided (as adjuvant therapy) along with other treatment modalities for brain tumors, which are selected based on location, the cell type and the grade of malignancy. Conventional therapies include surgery, radiation therapy, and chemotherapy. Temozolomide is a chemotherapeutic drug that is able to cross the blood-brain barrier effectively and is being used in therapy. For recurrent high-grade glioblastoma, recent studies have taken advantage of angiogenic blockers such as bevacizumab in combination with conventional chemotherapy, with encouraging results. Other agents include, but are not limited to, temodal, nitrosoureas, carmustine and cis-platin as well as antibody-based drugs, e.g., cetuximab.

Other Anti-cancer drugs that can be co-administered with the agents of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

It is expected that during the life of a patent maturing from this application many relevant enzyme and co-factor agents will be developed and the scope of the agents for lowering blood glu level is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", an and the include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Materials and Experimental Procedures

Animals—

Male SPD&OLD rats weighing 260-280 g were used and placed in individual cages. All experiments were conducted according to the guidelines of the institutional animal care and use committee of the Weizmann Institute of Science, Rehovot, Israel.

Cell Cultures—

The rat glioma cell line C6 (ATCC Accession Number CCL-107) was cultured (10 ml in a T-25 $cm^2$ flask) in DMEM supplemented with 10% FBS, 0.1 mg/ml kanamycin, and 4 mg/ml glucose at 37° C. under a humidified atmosphere of 5% CO2, 95% air. Glioma cells were subcultured every 3-4 days. For each experiment, confluent monolayers of cells were released from the tissue culture flask using 0.25% trypsin and rinsed twice with serum-free RPMI-1640. Cells were cultured in 96-well plates ($20\times10^3$/0.2 ml/well) or in 12-well plates ($160\times10^3$/3 ml/well) for the determination of cell viability and proliferation. Following an overnight adherence period, the 96-well cultured cells were rinsed twice with serum-free RPMI-1640 and then treated with either vehicle or oxaloacetate for 24-72 h (4 wells/treatment group). Cell number was determined using hemocytometer.

Intrastriatal Implantation

Rat C6 glioma cells were grown in DMEM medium supplemented with 10% FCS. $10^7$ cells were plated on 100× 20 mm dishes and grown to 80% confluence for two days, passaged at a dilution of 1:10 after 1-2 min exposure to 0.25 trypsin and plated on 7 plates 60×15 mm. The cells were grown to 80% confluence for two additional days. The cells were then trypsynized as above, washed once with sterile PBS and centrifuged for 15 min at 1200 rpm. Prior to centrifugation, the cells were counted in a hemocytometer. Following centrifugation, the medium was removed and the cells were diluted in sterile PBS to a final concentration $1\times10^4$/ml and 1 ml was injected immediately intracranially. For that purpose, the rats were anesthetized with 1.5% Halothane and placed in a stereotactic apparatus.

The glioma cells were slowly injected over 20 min into a 0.5 mm pocket made with a 23-gauge needle in the left anterior corpus striatum (0 mm bregma, +3 mm left lateral, 5.5 mm depth). In some cases, rats received also a subcutaneous injection. In that case, $1\times10^6$ glioma cells were injected in the chest area.

Treatment Protocol—

The treatment protocol comprised providing the rats (each rat was placed into an individual cage) with drinks consisting of 0.2M oxaloacetate or NaCl; The control group consisted of rats offered 50 ml/day of 0.4M NaCl in tap water. The experimental group consisted of rats offered 50 ml/day of 0.2M oxaloacetate sodium salt in tap water. The reason for the apparent difference in concentration is due to the fact that the solution of sodium oxaloacetate is extremely acidic and has to be neutralized by an equivalent amount of NaOH in order to reach neutral pH values.

MRI Analysis—

Experiments on live animals were conducted on a Biospec Avance™ system (Bruker Biospin, Ettlingen, Germany) with a 4.7 T 30-cm horizontal bore magnet. For the experiments described here, the main actively shielded 20-cm i.d. gradient coil was used with a maximal intensity of 100 mT/m and 0.33-ms rise time. The RF probe system included a 7.5-cm resonator for pulse transmission and a 2.5-cm circular receive-only surface coil with active detuning between the transmit and receive coils. MRI analysis of the growth of a C6 glioma implanted in rat brain striatum was performed using a Sequential T2-W and gadolinium-enhanced T1-W images in the tumor region. For the T1-W images, 0.5 ml of Dotarem (gadoteric acid 27.932 g, DOTA 20.246 g, gadolinium oxide 9.062 g per 100 ml of solution) was injected intravenously. The parameters for image acquisition were: time of repetition=2000 ms, echo time=54 ms, field of view=4.0 cm, matrix size=256×256, slice thickness 1.0 mm, slice gap between center to-center of consecutive slices=1.2 mm. The volume of the tumor was assessed using the Surdriver program Results Oxaloacetate does not Affect Glioma Cells In Vitro—

Figure 1:
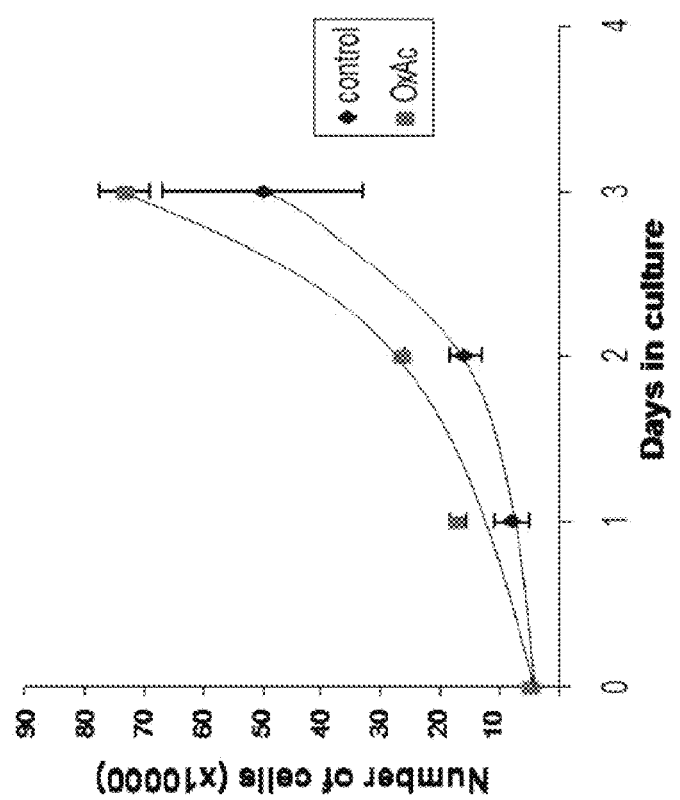

To test the effect of oxaloacetate (OA) on glioma cells in vitro, C6 glioma cells were incubated with 1 mM oxaloacetate. Since oxaloacetate solutions are unstable, the cell culture medium was changed every day to allow the cells to be daily exposed to a fresh oxaloacetate solution. As can be seen from FIG. 1, viability and proliferative status of the glioma cells was not affected by OA.

Oxaloacetate Retards Glioma Spread In Vivo—

After establishing that oxaloacetate has no effect on glioma growth when grown under in vitro conditions, the effect of same in vivo was determined. For that purpose, C6 glioma cells were implanted into the rat striatum. Tumor development was followed using MRI T1 and T2 imaging. FIGS. 2a-b show an example of tumor growth in an oxaloacetate-treated rat. Tumor spread was in average at least 10 folds less than that of untreated animals that received drinking water only (not shown). The results on two groups of 19 rats are shown in FIG. 3. Clearly, OA retards tumor invasivenss in a significant manner.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited Throughout the Application

Arcella A, Carpinelli G, Battaglia G, D'Onofrio M, Santoro F, Ngomba R T, Bruno V, Casolini P, Giangaspero F, Nicoletti F. (2005): Pharmacological blockade of group II metabotropic glutamate receptors reduces the growth of glioma cells in vivo. Neuro Oncol 7(3):236-45.

Berl S, Lajtha A, Waelsch H. (1961): Amino acid and protein metabolism of the brain. VI. Cerebral compartments of glutamic acid metabolism. J Neurochem 7( ):186-197.

Birmingham K. (2002): Future of neuroprotective drugs in doubt. Nat Med 8(1):5.

Gottlieb M, Wang Y, Teichberg V I. (2003): Blood-mediated scavenging of cerebrospinal fluid glutamate. J Neurochem 87(1):119-26.

Ikonomidou C, Turski L. (2002): Why did NMDA receptor antagonists fail clinical trials for stroke and traumatic brain injury? Lancet Neurol 1(6):383-6.

Ishiuchi S, Tsuzuki K, Yoshida Y, Yamada N, Hagimura N, Okado H, Miwa A, Kurihara H, Nakazato Y, Tamura M and others. (2002): Blockage of Ca(2+)-permeable AMPA receptors suppresses migration and induces apoptosis in human glioblastoma cells. Nat Med 8(9):971-8.

Lutsep H, Clark W. (2001a): An update of neuroprotectants in clinical development for acute stroke. Curr Opin Investig Drugs 2(12):1732-6.

Lutsep H L, Clark W M. (2001b): Current status of neuroprotective agents in the treatment of acute ischemic stroke. Curr Neurol Neurosci Rep 1(1):13-8.

Lyons S A, Chung W J, Weaver A K, Ogunrinu T, Sontheimer H. (2007): Autocrine glutamate signaling promotes glioma cell invasion. Cancer Res 67(19):9463-71.

O'Kane R L, Martinez-Lopez I, DeJoseph M R, Vina J R, Hawkins R A. (1999): Na(+)-dependent glutamate transporters (EAAT1, EAAT2, and EAAT3) of the blood-brain barrier. A mechanism for glutamate removal. J Biol Chem 274(45):31891-5.

Pawlik G, Rackl A, Bing R J. (1981): Quantitative capillary topography and blood flow in the cerebral cortex of cats: an in vivo microscopic study. Brain Res 208(1):35-58.

Rzeski W, Ikonomidou C, Turski L. (2002): Glutamate antagonists limit tumor growth. Biochem Pharmacol 64(8):1195-200.

Sheline C T, Behrens M M, Choi D W. (2000): Zinc-induced cortical neuronal death: contribution of energy failure attributable to loss of NAD(+) and inhibition of glycolysis. J Neurosci 20(9):3139-46.

Sontheimer H. (2003): Malignant gliomas: perverting glutamate and ion homeostasis for selective advantage. Trends Neurosci 26(10):543-9.

Takano T, Lin J H, Arcuino G, Gao Q, Yang J, Nedergaard M. (2001): Glutamate release promotes growth of malignant gliomas. Nat Med 7(9):1010-5.

Teichberg V I, Cohen-Kashi-Malina K, Cooper I, Zlotnik A. (2008): Homeostasis of glutamate in brain fluids: An accelerated brain-to-blood efflux of excess glutamate is produced by blood glutamate scavenging and offers protection from neuropathologies. Neuroscience.

Ye Z C, Rothstein J D, Sontheimer H. (1999): Compromised glutamate transport in human glioma cells: reduction-mislocalization of sodium-dependent glutamate transporters and enhanced activity of cystine-glutamate exchange. J Neurosci 19(24):10767-77.

Ye Z C, Sontheimer H. (1999): Glioma cells release excitotoxic concentrations of glutamate. Cancer Res 59(17):4383-91.

Zlotnik A, Gurevich B, Cherniaysky E, Tkachov S, Matuzani-Ruban A, Leon A, Shapira Y, Teichberg V I. (2008): The contribution of the blood glutamate scavenging activity of pyruvate to its neuroprotective properties in a rat model of closed head injury. Neurochem Res 33(6):1044-50.

What is claimed is:

1. A method of treating a glioma in a subject in need thereof, the method comprising intravenously administering to the subject as an adjuvant treatment for said glioma, a therapeutically effective amount of an agent being at least one glutamate modifying enzyme selected from the group consisting of glutamate oxaloacetate transaminase and glutamate pyruvate transaminase, which reduces blood glutamate levels and enhances brain to blood glutamate efflux to thereby treat glioma in the subject.

2. A kit identified for treating a glioma comprising a unit dosage form comprising, as the active ingredient at least one glutamate modifying enzyme selected from the group consisting of glutamate oxaloacetate transaminase and glutamate pyruvate transaminase, a chemotherapeutic agent approved by the FDA, and a pharmaceutically acceptable carrier, wherein said unit dosage form is formulated for intravenous administration to a human subject as an adjuvant treatment for said glioma, wherein the kit comprises instructions for administration of said unit dosage form to the subject and wherein said glutamate modifying enzyme is capable of reducing blood glutamate levels and enhancing brain to blood glutamate efflux and said chemotherapeutic agent is able to cross the blood brain barrier.

3. The method of claim 1, wherein the agent further comprises at least one co-factor of a glutamate modifying enzyme.

4. The method of claim 3, wherein the co-factor is selected from the group consisting of oxaloacetate and pyruvate.

5. The method of claim 3, wherein the glutamate modifying enzyme comprises glutamate oxaloacetate transaminase and the co-factor thereof comprises oxaloacetate.

6. The method of claim 3, wherein the glutamate modifying enzyme comprises pyruvate transaminase and the co-factor thereof comprises pyruvate.

7. The kit of claim 2, wherein said chemotherapeutic agent which is able to cross the blood brain barrier comprises Temozolomide.

8. The kit of claim 7, wherein the glutamate modifying enzyme comprises glutamate oxaloacetate transaminase.

9. The method of claim 5, further comprising administering to the subject a chemotherapeutic agent which is able to cross the blood brain barrier.

10. The method of claim 9, wherein said chemotherapeutic agent is Temozolomide.

\* \* \* \* \*